US010821070B2

(12) United States Patent
Griffiths et al.

(10) Patent No.: US 10,821,070 B2
(45) Date of Patent: Nov. 3, 2020

(54) METHOD AND KIT FOR RECONSTITUTING COSMETICS

(71) Applicants: Tess Griffiths, Los Angeles, CA (US); Barbara Villegas, West Hollywood, CA (US)

(72) Inventors: Tess Griffiths, Los Angeles, CA (US); Barbara Villegas, West Hollywood, CA (US)

( * ) Notice: Subject to any disclaimer, the term of this patent is extended or adjusted under 35 U.S.C. 154(b) by 236 days.

(21) Appl. No.: 15/989,918

(22) Filed: May 25, 2018

(65) Prior Publication Data

US 2019/0358147 A1 Nov. 28, 2019

(51) Int. Cl.
*A45D 33/00* (2006.01)
*B29C 43/36* (2006.01)
(Continued)

(52) U.S. Cl.
CPC ............ *A61K 8/9789* (2017.08); *A45D 33/00* (2013.01); *A61K 8/046* (2013.01); *A61K 8/34* (2013.01); *A61K 8/602* (2013.01); *A61K 8/678* (2013.01); *A61K 8/9794* (2017.08); *A61Q 19/00* (2013.01); *B29C 43/02* (2013.01); *B29C 43/36* (2013.01); *B29C 44/02* (2013.01);
(Continued)

(58) Field of Classification Search
None
See application file for complete search history.

(56) References Cited

U.S. PATENT DOCUMENTS 1,711,798 A * 5/1929 Kronish ............... A45D 33/006
264/120
1,731,219 A 10/1929 Atwood
(Continued)

FOREIGN PATENT DOCUMENTS

| KR | 300756487.0000 | 8/2014 |
| KR | 300756488.0000 | 8/2014 |
| KR | 300931268.000 | 11/2017 |

OTHER PUBLICATIONS

Steel Tamping and Digging Bar, Bully Tools, homedepot.com, author unlisted, posted Oct. 11, 2014 per wayback machine; available at URL: https:www.homedepot.com/p/Bully-Tools-48-in-Steel-Tamping-and-Digging-Bar-9244 (Year: 2014).
(Continued)

*Primary Examiner* — Jacob T Minskey
*Assistant Examiner* — Baileigh Kate Darnell
(74) *Attorney, Agent, or Firm* — Eric Kelly (57) ABSTRACT

A method and kit for reconstituting broken fragments of a cosmetic, such as pressed powder cosmetics, are provided which enable a user to recombine or reconstitute such fragments in the original cosmetic packaging. The kit comprises a foamable liquid composition, spreading implement, and at least one pressing implement. Applying embodiments of the foamed liquid composition on fragmented cosmetic material, pressing or packing the mixture comprising the liquid composition and fragmented cosmetic material, and then smoothing the composition by pressing it again within its original casing, in accordance with embodiments of the method, may avoid wasting broken cosmetic fragments and
(Continued)

further allows a consumer to use the reconstituted cosmetic for its original purpose.

18 Claims, 4 Drawing Sheets

(51) Int. Cl.
*A61K 8/9789* (2017.01)
*A61K 8/34* (2006.01)
*A61K 8/60* (2006.01)
*A61K 8/04* (2006.01)
*A61K 8/9794* (2017.01)
*A61K 8/67* (2006.01)
*B29C 43/02* (2006.01)
*B29C 44/02* (2006.01)
*B29C 44/56* (2006.01)
*A61Q 19/00* (2006.01)
*B29L 31/00* (2006.01)
*B29K 105/26* (2006.01)

(52) U.S. Cl.
CPC ...... *B29C 44/5627* (2013.01); *B29K 2105/26* (2013.01); *B29L 2031/718* (2013.01)

(56) References Cited

U.S. PATENT DOCUMENTS

| | | | |
|---|---|---|---|
| 2,074,795 A | 3/1937 | Mantelet | |
| 2,994,262 A | 8/1961 | Bator | |
| 3,222,030 A | 12/1965 | Thorpe | |
| D223,689 S | 5/1972 | Forbes | |
| D232,280 S | 8/1974 | Bingham | |
| D249,910 S | 10/1978 | Cottrell | |
| D249,911 S | 10/1978 | Cottrell | |
| 4,337,859 A * | 7/1982 | Murphy | A45D 33/00 132/294 |
| D283,856 S | 5/1986 | Elmaleh | |
| D295,004 S | 4/1988 | Schulz | |
| D298,597 S | 11/1988 | Bell | |
| D319,556 S | 9/1991 | Purkapile | |
| D338,310 S | 8/1993 | Clarke | |
| D340,822 S | 11/1993 | Morand | |
| D341,856 S | 11/1993 | Silverman | |
| D395,987 S | 7/1998 | Loughead | |
| D399,103 S | 10/1998 | Lillelund | |
| D404,947 S | 2/1999 | Porcelli | |
| D408,687 S | 4/1999 | Chan | |
| D432,828 S | 10/2000 | Snell | |
| 6,245,341 B1 * | 6/2001 | Pahlck | A45D 33/00 424/401 |
| 6,257,247 B1 * | 7/2001 | Benzinger | A61Q 9/02 132/200 |
| D446,979 S | 8/2001 | Schultz | |
| 6,358,448 B1 * | 3/2002 | Green | A45D 33/006 264/109 |
| D455,948 S | 4/2002 | Zetsche | |
| D457,271 S | 5/2002 | Jackson | |
| D459,623 S | 7/2002 | Tramontina | |
| D470,759 S | 2/2003 | Thorne | |
| 6,612,533 B2 | 9/2003 | Biles | |
| D485,742 S | 1/2004 | Heberle | |
| D498,099 S | 11/2004 | Chen | |
| D504,307 S | 4/2005 | Dayan | |
| D531,863 S | 11/2006 | Irwin | |
| D540,585 S | 4/2007 | Igarashi | |
| D545,343 S | 6/2007 | Braun | |
| D549,085 S | 8/2007 | Mevissen | |
| D567,023 S | 4/2008 | Baldieri | |
| D610,869 S | 3/2010 | Pourounidis | |
| D625,528 S | 10/2010 | Sprague | |
| D693,596 S | 11/2013 | Zeng | |
| D707,056 S | 6/2014 | Gilbert | |
| D718,896 S | 12/2014 | Foley | |
| D754,401 S | 4/2016 | Seiler | |
| D765,262 S | 8/2016 | Greenhouse | |
| D776,453 S | 1/2017 | Cross | |
| D815,167 S | 4/2018 | Lin | |
| D821,598 S | 6/2018 | Greenhouse | |
| D821,599 S | 6/2018 | Greenhouse | |
| 10,004,938 B2 | 6/2018 | Greenhouse | |
| D823,624 S | 7/2018 | Elmaleh | |
| 10,405,633 B2 * | 9/2019 | Rossini | B29C 43/36 |
| 2003/0235470 A1 | 12/2003 | Gelb | |
| 2005/0067435 A1 * | 3/2005 | Gentile | B05B 11/3087 222/190 |
| 2013/0234351 A1 * | 9/2013 | Johnson | A61Q 19/00 264/36.1 |
| 2015/0238409 A1 * | 8/2015 | Eizen | A61K 8/922 424/602 |
| 2015/0252291 A1 * | 9/2015 | Levine | A61L 9/013 512/2 |
| 2017/0065515 A1 * | 3/2017 | Karam | A61K 8/9789 |
| 2017/0127792 A1 * | 5/2017 | Rossini | B29C 43/36 |
| 2017/0223972 A1 | 8/2017 | Hotz | |

OTHER PUBLICATIONS

Square and Rectangle Pedestal Base, David Lane Office Furniture, Ltd., davidlane.com, author not listed, posted Apr. 2, 2018 per wayback machine. Available from Internet, URL: https://www.davidlane.com/metal/ (Year: 2018).

* cited by examiner

METHOD AND KIT FOR RECONSTITUTING COSMETICS

GOVERNMENT CONTRACT

Not applicable.

CROSS-REFERENCE TO RELATED APPLICATIONS

Not applicable.

STATEMENT RE. FEDERALLY SPONSORED RESEARCH/DEVELOPMENT

Not applicable.

COPYRIGHT & TRADEMARK NOTICES

A portion of the disclosure of this patent document may contain material which is subject to copyright protection. This patent document may show and/or describe matter which is or may become trade dress of the owner. The copyright and trade dress owner has no objection to the facsimile reproduction by any one of the patent document or the patent disclosure, as it appears in the Patent and Trademark Office patent files or records, but otherwise reserves all copyrights and trade dress rights whatsoever.

TECHNICAL FIELD

The disclosed subject matter relates generally to cosmetics preparations and, more particularly, to a kit and method for reconstituting broken powdered cosmetics.

BACKGROUND

Cosmetics are popular across many demographics as a means for recreationally and professionally augmenting and even sometimes changing one's appearance. As a result, there are countless varieties of cosmetics available in the marketplace, including cosmetics comprising powdered compositions pressed into and further stored in shallow pans. These cosmetics are frequently sold to consumers stored in closeable compact containers, which may be conveniently configured for storage and transportation in a purse or pocket, drawers, and the like.

Though common, collections of cosmetics can be relatively expensive to acquire and maintain. In some instances, desirable ingredients and/or brand recognition may increase the cost of these cosmetics. Some compositions may be pressed in to aesthetic, vanity compacts in an effort to provide cosmetics fit for display. Additionally, many cosmetics are configured to serve individual purposes. That is, cosmetic foundation known in the art, for example, is not typically formulated to also serve as eyeshadow or blush, and vice versa. This requires consumers to buy various types of cosmetics, often in a variety of different shades, to complete her entire beauty regimen.

Of course, regardless of cost, cosmetic compositions are rarely, if ever, immune from damage. For example, pressed powder cosmetics arranged in compacts commonly available on the marketplace have been known to shatter, become undesirably fragmented, or otherwise become loosened when dropped or struck. This damage can make the cosmetic difficult to use. For example, applying a makeup brush or other implement to a broken powder cosmetic may cause a user to draw too much of the cosmetic product onto their implement. This may negatively affect application of the product on the skin. As just one example of a result, a user may inadvertently apply too much of the cosmetic to their face, which may cause their appearance to be unintentionally blotchy or overly pigmented. In some cases, fragmented portions of a pressed powder cosmetic may even fall entirely out of its pan, making a mess of nearby surfaces and contaminating the fallen portions. This may render the powder unusable and lower the shelf-life of the original product.

Some solutions have been proposed to solve the problem of broken pressed powder cosmetics. One exemplary proposal has been to repurpose the broken pieces of pressed powder cosmetics. For instance, compacted powder blush, typically marketed for application to the cheeks as a rouge, may be made into a creamy gloss or balm by mixing crushed pieces with some amount of petroleum jelly or other emollient compositions. The same may be done for pressed powder eyeshadows. This can be a beneficially frugal way of avoiding waste, however, it is obviously deficient for the fact that a consumer may no longer use the original cosmetic in the manner it was prescribed.

Some solutions have been proposed to reconstitute and therefore prolong the life of a shattered compact makeup as originally marketed and/or sold. For instance, some knowledgeable in the art recommend fully removing broken pressed powder from its pan, crushing it further, then mixing the crushed cosmetic with rubbing alcohol, vodka, or surgical spirits. Once mixed, a paste like slurry can be returned to and smoothed in the pan. Then, the slurry may be left exposed to the air so that any liquid may evaporate, leaving behind a reconstituted, pressed powder cosmetic. Related teachings may be seen in U.S. Pat. No. 1,968,475 to Beckwith et al. and U.S. Pat. Pub. No. 2012/0286441 filed by Johnson.

These proposals have a variety of deficiencies. For instance, the references suggest incorporating alcohol with the cosmetic powder and fragments to create a paste-like slurry. However, it may be inconvenient or difficult to mix ingredients to create a slurry within a small pan and also avoiding dropping, contaminating, or otherwise wasting any of the material.

Another proposal to solve the problem of wasting broken pressed powder cosmetics has been to recompact the fragments together in the shallow pan by applying, variously, heat and pressure to the fragments. Of course, applications of heat may be dangerous to the consumer and may further, undesirably, melt or burn ingredients comprising the cosmetic. Forcibly reconstituting the pressed powder may cause damage to the storage pan and/or case and may not sufficiently bind the loosened fragments.

Although proposals for using and repairing broken cosmetic fragments have been suggested, all of those heretofore known suffer from a number of disadvantages. As such, there remains a need for a method and kit for reconstituting pressed powder cosmetics so that they may be useable in their original form and packaging.

SUMMARY

The present disclosure is directed to a method and kit for repairing broken or fragmented cosmetics. In some embodiments, the method and kit may be applied to crème cosmetics such as lipsticks, eyeliners, eyeshadows, foundation, concealer, and blush, among others and even to loose, pigmented powders which one may use to create one's own powder cake cosmetics. Although embodiments of the kit and method may be widely applicable to constitute a variety of cosmetics, they will be discussed in relation to repairing powder cosmetics for the sake of brevity and example only. In particular, the method, making use of elements comprising the kit, may beneficially enable a person to apply a liquid composition to fragmented cosmetic powders while avoiding any need to remove such powder from its original casing. Thus, the following should not be seen to limit the invention.

For purposes of summarizing, certain aspects, advantages, and novel features have been described. It is to be understood that not all such advantages may be achieved in accordance with any one particular embodiment. Thus, the disclosed subject matter may be embodied or carried out in a manner that achieves or optimizes one advantage or group of advantages without achieving all advantages as may be taught or suggested.

In accordance with one embodiment, a kit for reconstituting cosmetics may comprise a liquid composition, a dispenser for the liquid composition, a spreading implement, and a pressing implement.

An exemplary method for reconstituting cosmetics may comprise the following, exemplary, steps. Salvageable fragments, including any loosened powder particles, of a pressed powder or other type of cosmetic may be gathered and swept into any pan or other packaging provided with the cosmetic. In some embodiments a person may use his or her own finger, spoon, knife, or other convenient implement to gather and sweep fragments and loosened powder particles of the broken cosmetic into the pan or other packaging. However, it is contemplated, that providing a spreading implement to do so may prevent a person from unwittingly introducing germs and other undesirable material from his or her fingers directly into the powdered fragments and particles. Using a spreading implement, such as a broad and flat spatula having a smooth outer edge, to gather and sweep the fragments and loosened particles may help avoid adding oils and bacteria from one's fingers to the fragments and loosened particles during the sweeping step.

Next, the cosmetic, including swept particles and fragments, may be further broken into smaller pieces. This may be done, for example and not limitation, by using the edge of the spatula or other spreading implement as a knife to forcibly break the cosmetic within the pan. Then, a pressing implement may be used to press the upper surface of the broken cosmetic into a relatively level, flat surface. In some embodiments, the pressing implement is a tamper comprising a handle terminating in a broad, flat face operative to distribute downward pressing force over a surface beneath the face. It is contemplated that pressing the cosmetic into a relatively flat surface before moistening the cosmetic may ensure that any need to physically incorporate the liquid composition into fragmented product, such as by mixing with the spatula, or even any need to spread the mixture is avoided.

Then, the liquid composition for reconstituting cosmetics may be dispensed over the affected area of the fragmented—but gathered—cosmetic. That is, it is contemplated that only a portion of the cosmetic may have been broken or fragmented. In some embodiments then, it may be possible to effectively perform the method by moistening an upper surface of only the broken or fragmented portions of the cosmetic powder. This may beneficially avoid wasteful application of the liquid composition. In some embodiments, however, it may be desirable to more uniformly imbue the cosmetic powder with the liquid composition. Thus, in some embodiments, the liquid composition may be applied to the entire upper surface of the cosmetic powder.

The liquid composition may be dispensed from a foaming container so that the composition may be applied as a vast plurality of small bubbles all over the cosmetic. This may ensure that both fragmented cosmetic materials as well as the liquid composition may be maintained in a relatively contained area, again reducing possible waste of the composition and maintaining a relatively clean working area.

In some embodiments, the composition comprising the method and kit for reconstituting cosmetics comprises only about 10% to about 30% by weight of alcohol, such as ethanol, grain alcohol, or even isopropyl alcohol. Alcohol may be beneficial as a volatile liquid that readily evaporates at normal temperatures and even further comprises anti-bacterial properties. Thus, when applied to, for example, pressed powder cosmetics, it may effectively kill bacteria which may have become mixed in cosmetic particles and further evaporate from any mixture to provide a reconstituted pressed powder. However, use of alcohol alone involves a variety of deficiencies, such as skin-drying and pro-aging properties, and may leave cosmetic compositions brittle when used to reconstitute them. Therefore, in order to avoid an overabundance of alcohol, *Hamamelis virginiana*, more commonly known as witch hazel, may be provided in amounts from about 70% to about 90% of the composition by weight.

Witch hazel may comprise tannins, volatile oils, humectants, antioxidants, and anti-bacterial, anti-fungal, and anti-inflammatory properties as its primary active ingredients, which contribute to its astringent and other benefits. The ability of witch hazel to shrink or contract tissues, such as skin, may make its application in the field of cosmetics particularly desirous. Anti-fungal properties in particular may be desirous in preventing fungal growths from forming in reconstituted cosmetics.

Additionally, a foaming agent, wetting agent, or even surfactant may be provided in order to reduce the surface tension of liquids in the composition. In some embodiments, a surfactant may be provided as decyl glucoside in an amount of about 0.5% to about 5% of the composition by weight. Including a surfactant as an element comprising the composition element of the method and kit described herein may enable the composition to break up residual oils in fragmented cosmetics, including pressed powders, and allow the pieces to be more evenly recombined. Additionally, including a foaming and/or wetting agent may configure the composition for convenient dispensation from a foaming dispenser. Decyl glucoside may be particularly desirable for this purpose due to the fact that it is relatively mild, plant-based, and even biodegradable. Of course, other foaming agents, or even surfactants, are known to those skilled in the art and may be used in combination with or instead of decyl glucoside. Thus, the foregoing is offered by way of example only and not limitation.

Additional beneficial ingredients may be provided in the composition comprising the method and kit for reconstituting powder cosmetics. For instance, in some embodiments, a pleasantly scented volatile oil, also known as an essential oil, may comprise the invention to improve any smell associated with the composition. As an example, in some embodiments, lavender oil may comprise about 0.01% to about 0.2% of the composition by weight. Of course, other pleasantly scented essential oils are known in the art and may be used instead or in addition to lavender oil. Additional carrier oils may be provided, such as jojoba oil and fractionated coconut oil, either alone or in combination with one another in amounts of about 0.01% to about 0.2% of the composition by weight, to prevent the essential oil from evaporating entirely from the reconstituted cosmetic. This may ensure that even once dried following application of the steps of the method for reconstituting cosmetics, the reconstituted cosmetic retains the pleasant scent of the volatile or essential oil. It is contemplated that these, along with any essential oils, may be provided in small amounts relative to the total weight of the composition so that general wetness of any reconstituted cosmetic material is avoided.

Vitamins and other minerals may be included in the liquid composition comprising the method and kit for reconstituting cosmetics as well. For instance, it may be desirable to include vitamin E in amounts of about 0.01% to about 0.2% of the composition by weight may also be provided as an additional ingredient in small amounts due to its anti-inflammatory, anti-oxidant, and UV protecting qualities.

The foamed embodiment of the liquid composition may be left to dissolve into a pressed cosmetic formulation, and in some embodiments, it may be desirable to repeat the steps of dispensing some of the liquid composition over the pressed cosmetic. This may be particularly desirable where it appears that some fragmented portion of the cosmetic has remained dry or is even cracking rather than reconstituting. Indeed, it is contemplated that failing to moisten parts of the cosmetic which have been further broken, gathered, and then pressed within the original pan, for example, may prevent the mixture from reconstituting into an apparently solid, packed powder cake.

Once pressed the smoothed, moistened cosmetic may be left exposed in a well-ventilated area for about 6 to about 24 hours or more so that the liquid composition, which has dissolved into at least the surface of the cosmetic, may evaporate and leave behind a relatively dry, reconstituted, cosmetic. It should be understood that some ingredients comprising the liquid composition, such as fragrance or essential oil, may not fully evaporate. This will not limit the invention.

After the cosmetic has been left exposed for an extended period of time, the pressing implement may be used again to press the upper surface of the cosmetic within the pan to smooth its surface.

Other steps may be practiced to provide the reconstituted cosmetic with a desirable aesthetic appearance such as cleaning the surface of the compact surrounding the pan of cosmetic debris and pressing or etching a design into the surface of the pressed cosmetic while damp. For example, a face of the tamper described above may include a patterned surface which imparts a desirable design into the surface of the pressed cosmetic.

One or more of the above-disclosed embodiments, in addition to certain alternatives, are provided in further detail below with reference to the attached figures. The disclosed subject matter is not, however, limited to any particular embodiment disclosed.

Several advantages of one or more aspects are to provide a cosmetic repair method and kit that:
  (a) prevents waste of cosmetic material;
  (b) avoids a need to remove cosmetic powder fragments in their original cosmetic pan and/or packaging for repair; and
  (c) achieves a clean appearance of the reconstituted cosmetic powder.

These and other advantages of one or more aspects will become apparent from consideration of the ensuing description and accompanying examples. Although the description above contains many specifics, these should not be construed as limiting the scope of the embodiments but as merely providing illustrations of some of several embodiments. Thus, the scope of the embodiments should be determined by the claims that the appended and their legal equivalents, rather than by the examples given.

The description of the invention which follows, together with the accompanying examples should not be construed as limiting the invention to the examples shown and described, because those skilled in the art to which this invention pertains will be able to devise other forms thereof within the ambit of the appended claims.

The disclosed embodiments may be better understood by referring to the figures in the attached drawings, as provided below. The attached figures are provided as non-limiting examples for providing an enabling description of the kit and method claimed. Attention is called to the fact, however, that the appended drawings illustrate only typical embodiments of this invention and are therefore not to be considered as limiting of its scope. One skilled in the art will understand that the invention may be practiced without some of the details included in order to provide a thorough enabling description of such embodiments. Well-known structures and functions have not been shown or described in detail to avoid unnecessarily obscuring the description of the embodiments.

DETAILED DESCRIPTION

Illustrative embodiments of the invention are described below. The showings are for purposes of illustrating preferred embodiments and not for purposes of limiting the same. The following explanation provides specific details for a thorough understanding of an enabling description for these embodiments. One skilled in the art will understand that the invention may be practiced without such details. In such instances, well-known structures and functions have not been shown or described in detail to avoid unnecessarily obscuring the description of the embodiments.

Figure 1:
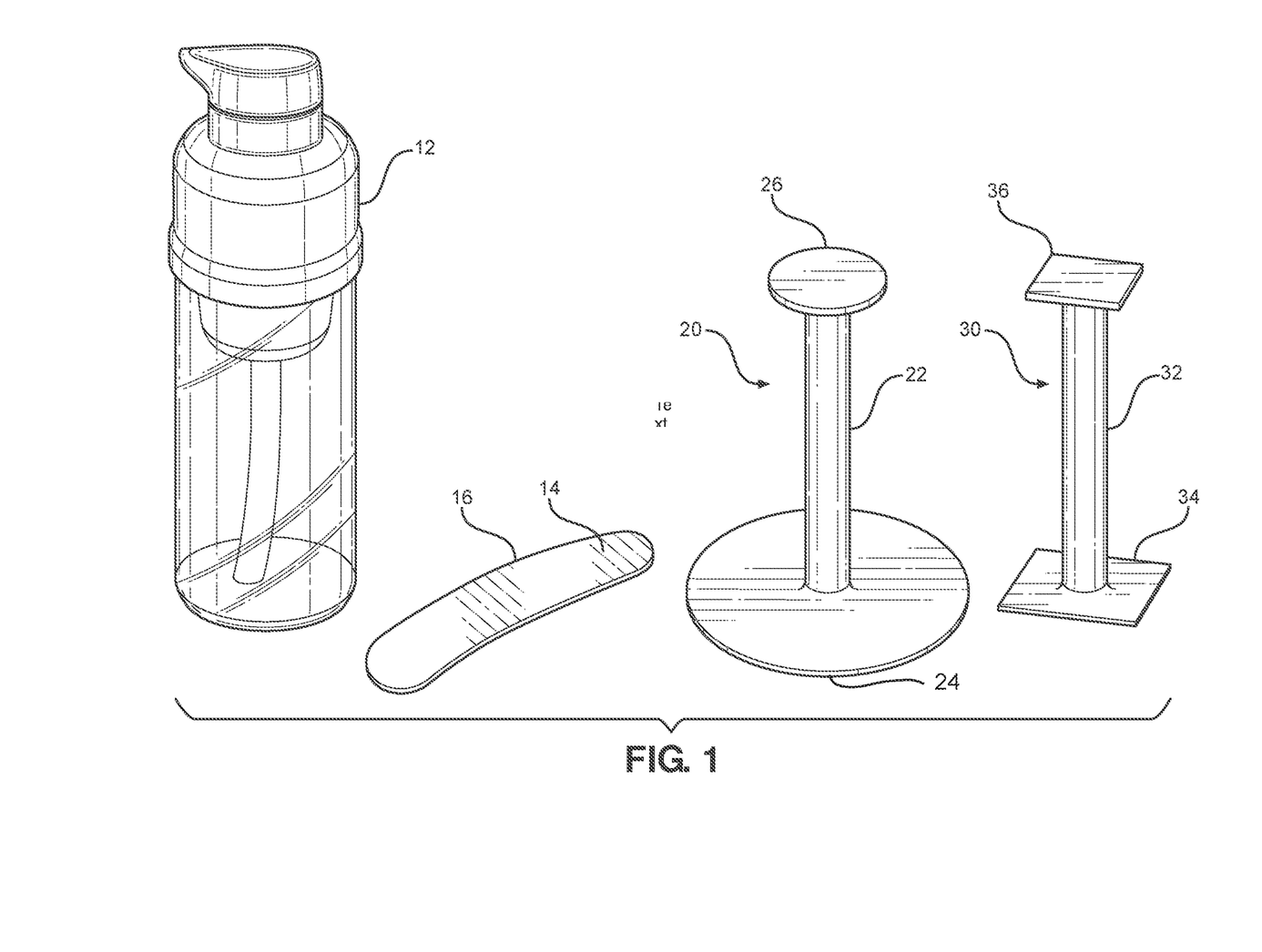
FIG. 1 shows elements comprising a kit for reconstituting cosmetics in accordance with one embodiment of the invention.

Referencing FIG. 1, an embodiment of a kit for reconstituting broken or fragmented cosmetics may comprise a liquid composition, a dispenser for the liquid composition, a spreading implement, and a pressing implement. More particularly, the dispenser may be a foaming pump bottle 12 of any desirable volume. Indeed, the bottle 12 may also be configured from a variety of materials such as thermoplastic polymer resins, other plastic materials, and even glass, for example, to contain and dispense about 2 fluid ounces to about 8 fluid ounces, or more or less, of the liquid composition.

The spreading implement may comprise a spatula 14 defining a smooth outer edge 16. In some embodiments, the edge 16 may be curved. In some embodiments, the edge may be straight. The spatula may be about 3 inches to about 8 inches long and about 0.5 inches to about 2 inches wide, though the particular dimensions and shape of the edge should not be seen to limit the invention. In some embodiments, a portion of the spatula 14 may be concave. Curving the edge 16 and/or providing a concave portion may enable a user to more easily gather, sweep, cut, and/or spread broken, fragmented, or even solid cosmetic material in accordance with certain embodiments of the method, which will be described in detail below. The spatula 14 may comprise any desirable material such as plastic, wood, metal, or glass and as such should not be limited.

The at least one pressing implement may be a tamper 20 having a grip 22 terminating in at least a first face 24. In addition, the grip 22 of the tamper 20 may terminate in an additional second face 26. It may be seen that exemplary first face 24 and second face 26 are round, and further that the second face 26 is smaller in size than the first face 24. As a result, a person may be able to use the tamper 20 to press cosmetics in pans of variously sized, round pans. Moreover, a second tamper 30, having a grip 32 and at least first face 34, but also in some embodiments a second face 36 defining a different size from the first face 34 may be provided so that a person may have even more options for pressing cosmetics housed in differently shaped pans. For instance, it may be seen that each face 34, 36 of the second tamper 30 is angular, rather than round, and defines a quadrilateral. This may be a convenient shape for pressing cosmetics contained square or rectangular pans, which are commonly provided in the marketplace. Other shapes are, of course, contemplated. Additionally, the tampers may comprise any convenient size and/or material, including plastic, wood, metal, glass, and combinations of the same. Thus, the foregoing has been offered by way of example only, and not limitation.

Figure 2:
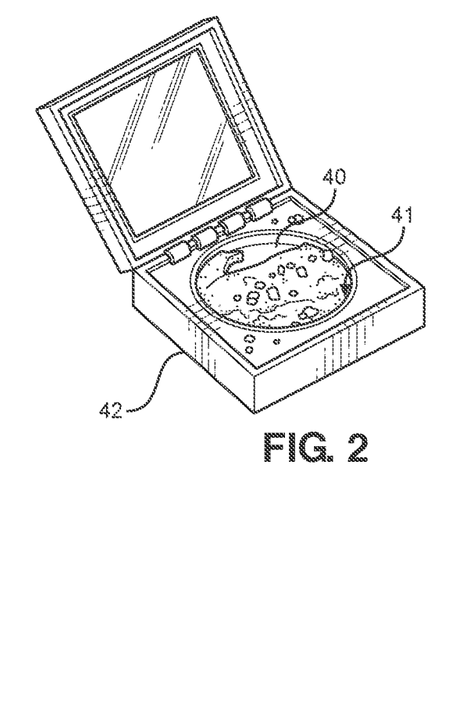
FIGS. 2-7 illustrate successive steps performed in a method for reconstituting cosmetics in accordance with one embodiment of the invention.

Referring now to FIG. 2, an exemplary method for reconstituting cosmetics will be discussed with particular reference to a cosmetic 40, such as any pressed powder cosmetics used as eyeshadow, blush, setting powder, and others, commonly provided in shallow pans stored within a conventional and closeable compact case 42. The method may also be used to reconstitute cream and other makeup compositions, thus, although a single pressed powder cosmetic 40 is stored in the case 42 depicted, it is to be understood that any number, type, or configuration of cosmetic formulations are contemplated. For instances, makeup palettes containing a plurality of shades and cosmetic compositions within a single compact case are popular in the marketplace. The disclosed kit and method may apply to those as well.

Figure 3:
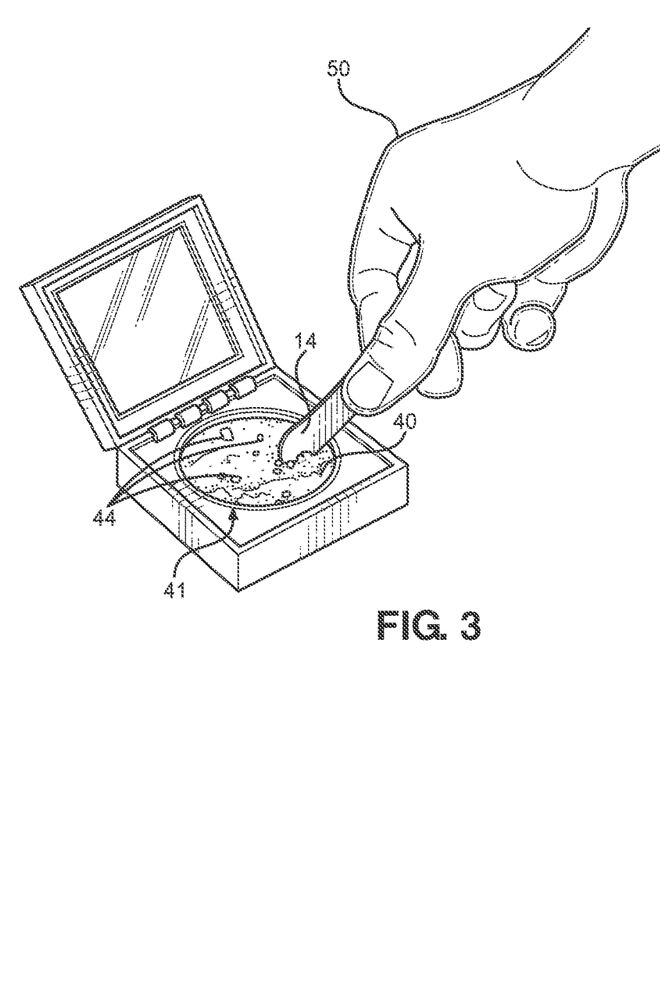

An exemplary method for reconstituting cosmetics may comprise the following, exemplary, steps. With reference to FIG. 3, it may first be seen that the exemplary powder cosmetic 40 appears jagged, or otherwise fragmented, and includes loose particles 44 on its upper surface. This may be generally undesirable because, for example, fragmented portions and loose particles may fall out of the pan 41, wasting cosmetic material, and making surfaces outside of the pan 41 dirty. Any of the fragmented portions of the powder cosmetic 40, including these loosened particles 44, may be gathered and swept into any pan 41 or other container provided to store the cosmetic. It should be noted that a person may alternatively choose to replace the cosmetic, or to even form a new cosmetic from loose powders, into a new pan, or after-market container as desired using the disclosed kit and method. In some embodiments a person 50 may use his or her own finger, spoon, knife, or other convenient implement to gather and sweep fragments and loosened particles 44 of the broken cosmetic into the pan or other packaging. However, it is contemplated that providing a spreading implement such as the spatula 14 to do so may prevent introduction of germs and other undesirable material from his or her fingers directly into the powdered fragments and particles. Additionally, the spatula 14 or other implement such as a butter knife, toothpick, spoon, awl may be used to further break up cosmetic 40 within the pan. Thus, it may be seen in FIG. 3 that spatula 14 is being used to slice into the cosmetic 40.

The spatula 14 or other spreading implement may also be used to superficially smooth broken fragments over an exposed upper surface of the cosmetic 40. Then, with reference to FIG. 4 a pressing implement may be used to forcibly press or pack the broken cosmetic 40 into the pan 41. It is contemplated that further breaking up cosmetic material within the pan before pressing may cause the cosmetic material to ultimately become more uniformly bound by the liquid composition because breaking up any underlying solid cosmetic may enable absorption of the liquid composition throughout the cosmetic 40.

Figure 5:
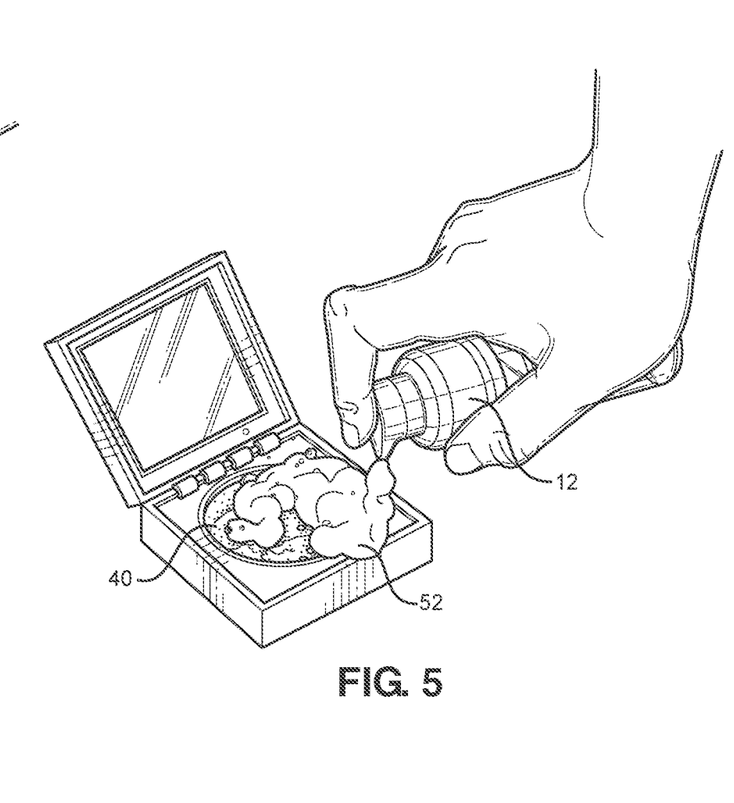

Then, with reference to FIG. 5, the liquid composition, here dispensed from the exemplary bottle 12 as a foam 52, may be dispensed over the affected area of the gathered fragments of cosmetic 40, which have been obscured by the foam 52. In some embodiments, it is contemplated that only a portion of the powder cosmetic may have been broken or fragmented. Thus, it may be possible to effectively perform the method by moistening a surface of only the broken or fragmented portions of the cosmetic 40. This may beneficially avoid wasteful application of the liquid composition. In some embodiments, however, it may be desirable to more uniformly imbue the cosmetic 40, or other cosmetic material as the case may be, with the liquid composition. Thus, in some embodiments, the liquid composition may be applied to the entire exposed surface of the cosmetic 40.

In some embodiments, the liquid composition may comprise witch hazel in combination with a volatile liquid, and a wetting agent for reducing surface tension in the composition. The wetting agent, or surfactant, may cause the liquid composition to be dispensable as a foam. In some embodiments, the volatile liquid is an alcohol provided in an amount up to about 30% by weight of the composition. In some embodiments, the wetting agent is decyl glucoside. Additionally, the composition may comprise additional ingredients such as fragrance, a carrier oil for the fragrance and even vitamins and/or minerals. These additional ingredients may include some or all of lavender essential oil, jojoba oil, fractionated coconut oil, and vitamin E, for example only and not limitation. As a more particular example, the composition may comprise *Hamamelis virginiana* in the amount of about 70.00 to about 90.00 wt. % of the exemplary composition; isopropyl alcohol or ethanol in the amount of about 10.00 to about 30.00 wt. % of the composition; decyl glucoside in the amount of about 0.50 to about 5.00 wt. % of the composition; lavender essential oil in the amount of about 0.01 to about 0.20 wt. % of the composition; jojoba oil in the amount of about 0.01 to about 0.20 wt. % of the composition; fractionated coconut oil in the amount of about 0.01 to about 0.20 wt. % of the composition; and vitamin E in the amount of about 0.01 to about 0.20 wt. % of the composition.

Ingredients comprising the liquid composition for reconstituting cosmetics may be dispensed on the cosmetic 40 in any amount so long as some time after application to the broken cosmetic powder, in some embodiments about 6 to about 24 hours, such reconstituted cosmetic will be relatively dry to the touch and may be applied by a consumer as desired.

Figure 4:
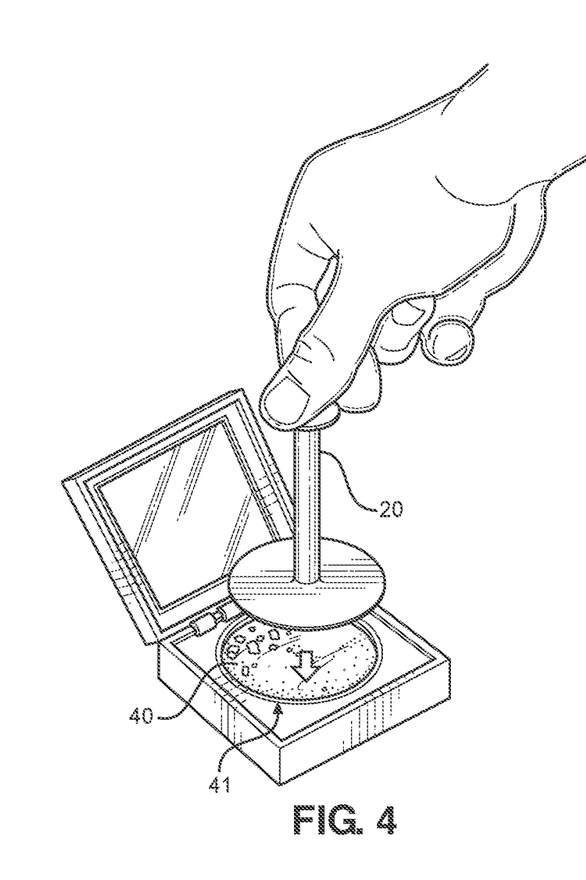

Once the foamed embodiment of the liquid composition dissolves into cosmetic 40, the now-moistened cosmetic 40 may take on the texture of a paste-like substance. In some embodiments, the liquid composition and cosmetic 40 may be thoroughly mixed together within the pan 41 using the spreading implement. Indeed, an upper surface of the moistened cosmetic 40 substance may also be spread generally smooth via the spreading implement within the bounds of the pan 41, however, it is contemplated that packing the cosmetic 40 as illustrated in FIG. 4 may avoid any need to perform a spreading step.

In some embodiments, it may be desirable to repeat either or both of the steps of further breaking cosmetic 40 material within the pan 41 and dispensing some of the liquid composition over the cosmetic 40, particularly where it appears that some fragmented portion of the cosmetic 40 has remained dry or is even cracking rather than reconstituting. Indeed, it is contemplated that failing to moisten fragmented parts of the cosmetic 40 gathered within the pan 41 may prevent the mixture from reconstituting into its original form.

Once moistened to the satisfaction of the person performing the method, the packed and moistened cosmetic may be left exposed in a ventilated area for about 6 to about 24 hours so that the liquid composition, which has dissolved into at least the surface of the cosmetic, may evaporate and leave behind a relatively dry, reconstituted, pressed cosmetic formulation. It should be understood that some ingredients comprising the liquid composition, such as fragrance or essential oil, may not fully evaporate. This will not limit the invention.

Figure 6:
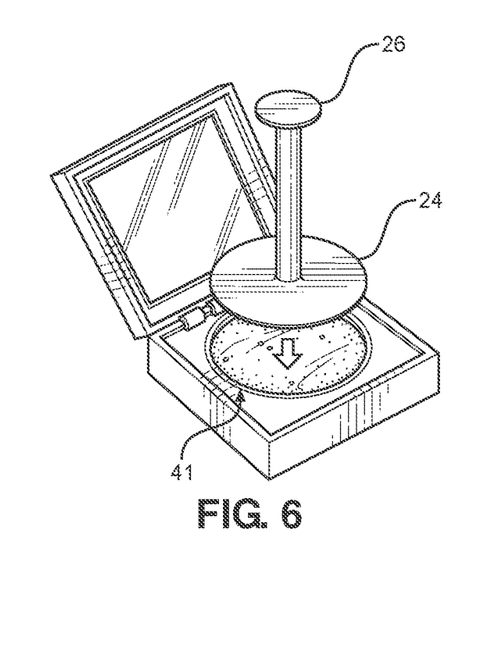
Figure 7:
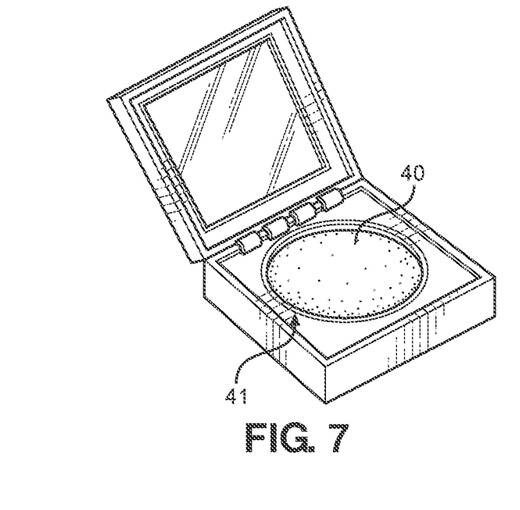

Turning to FIG. 6, once the cosmetic is dry to the satisfaction of a person reconstituting the cosmetic, for example, once the cosmetic feels dry or powdery to the touch, a person may again use the tamper 20, or other pressing implement, to apply a downward force on the surface of the relatively dry cosmetic 40 via one of the first or second faces 24, 26. It is contemplated that this may forcibly bind the previously broken fragments and cause any pressed surface of the cosmetic 40 to appear smooth within its pan 41, as shown in FIG. 7. Any face of the tamper 20 used to apply the downward force to the reconstituted cosmetic 40 may be selected depending on the particular shape and size of the pan 41 containing the cosmetic powder 41, although multiple shapes and sizes of faces may be applicable to variously configured cosmetic pans. For example, a face that is smaller than the surface area of the pan may be used to smooth discrete portions of cosmetic, while a face that is about the same side as the surface are of the pan, such as those shown in FIGS. 4 and 6 may be useful. In any event, using the tamper 20, or other pressing implement, to apply a downward force on the cosmetic 40 may allow a person to shape the cosmetic 40 so that it may define a relatively flat, reconstituted surface.

Other steps may be practiced to provide the reconstituted cosmetic with a desirable aesthetic appearance. Additional steps may include cleaning the surface of the compact surrounding the pan of cosmetic debris and pressing or etching a design into the surface of the pressed cosmetic while damp. For example, the face of the tamper described above may include a patterned surface which imparts a desirable design into the surface of the pressed cosmetic.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

CONCLUSIONS, RAMIFICATIONS, AND SCOPE

While certain embodiments of the invention have been illustrated and described, various modifications are contemplated and can be made without departing from the spirit and scope of the invention. Accordingly, it is intended that the invention not be limited, except as by the appended claim(s).

The teachings disclosed herein may be applied to other systems and may not necessarily be limited to any described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions and concepts of the various references described above to provide yet further embodiments of the invention.

Particular terminology used when describing certain features or aspects of the invention should not be taken to imply that the terminology is being refined herein to be restricted to any specific characteristics, features, or aspects of the kit and method for reconstituting cosmetics with which that terminology is associated. In general, the terms used in the following claims should not be constructed to limit the liquid composition for reconstituting cosmetics to the specific embodiments disclosed in the specification unless the above description section explicitly define such terms. Accordingly, the actual scope encompasses not only the disclosed embodiments, but also all equivalent ways of practicing or implementing the disclosed system, method and apparatus. The above description of embodiments of the liquid composition for reconstituting cosmetics is not intended to be exhaustive or limited to the precise form disclosed above or to a particular field of usage.

While specific embodiments of, and examples for, the method, system, and apparatus are described above for illustrative purposes, various equivalent modifications are possible for which those skilled in the relevant art will recognize.

While certain aspects of the method and system disclosed are presented below in particular claim forms, various aspects of the method, system, and apparatus are contemplated in any number of claim forms. Thus, the inventor reserves the right to add additional claims after filing the application to pursue such additional claim forms for other aspects of the liquid composition for reconstituting cosmetics.

What is claimed is:

1. A method for reconstituting broken cosmetic material back into non-fragmented cosmetic material, comprising steps of:
   (a) gathering and sweeping broken fragments of the broken cosmetic material into a pan that includes the non-fragmented cosmetic material;
   (b) breaking up the broken fragments of the broken cosmetic material within the pan into smaller broken fragments, wherein the smaller broken fragments and the non-fragmented cosmetic material are both dry and both residing within the pan;

(c) pressing a substantially flat surface downward onto the smaller broken fragments to pack the smaller broken fragments within the pan, wherein this pressing and packing of the step (c) occurs while the smaller broken fragments and the non-fragmented cosmetic material are both dry;

(d) dispensing a foam composition onto an upper surface of the smaller broken fragments that were pressed and packed according to the step (c), wherein the step (d) results in at least some of the smaller broken fragments dissolving, wherein the foam composition comprises, at least,
   i) *Hamamelis virginiana,*
   ii) a volatile liquid, and
   iii) a foaming agent;

(e) leaving a result of the step (d) to air dry for at least a predetermined amount of time, wherein the step (d) results in substantially all of the volatile liquid evaporating upon conclusion of the step (d); and f) pressing the substantially flat surface onto all of materials within the pan, that are now dry, resulting in the broken fragments being reconstituted into the non-fragmented cosmetic material such that there are substantially none of the smaller broken fragments remaining as the smaller broken fragments.

2. The method according to claim 1, wherein the foam composition comprises: the *Hamamelis virginiana* in about 70.00 to about 90.00 wt. % of the foam composition; isopropyl alcohol in about 10.00 to about 30.00 wt. % of the foam composition, wherein the isopropyl alcohol is the volatile liquid; and decyl glucoside in about 0.50 to about 5.00 wt. % of the foam composition, wherein the decyl glucoside is the foaming agent.

3. The method according to claim 1, wherein the foam composition further comprises a fragrance and at least one carrier oil for the fragrance.

4. The method according to claim 1, wherein the foam composition further comprises: lavender essential oil in about 0.01 to about 0.20 wt. % of the foam composition; jojoba oil in about 0.01 to about 0.20 wt. % of the foam composition; fractionated coconut oil in about 0.01 to about 0.20 wt. % of the foam composition; and vitamin E in about 0.01 to about 0.20 wt. % of the foam composition.

5. The method according to claim 1, wherein the method further comprises a step of mixing materials within the pan using a spreading implement, wherein this step occurs after the step (d) but before the step (e).

6. The method according to claim 1, wherein the step (b) occurs after the step (a); wherein the step (c) occurs after the step (b); wherein the step (d) occurs after the step (c); wherein the step (e) occurs after the step (d); and wherein the step (f) occurs after the step (e).

7. The method according to claim 1, wherein the predetermined amount of time is a time selected from a range of six hours to twenty four hours.

8. A kit for reconstituting broken cosmetic material back into non-fragmented cosmetic material within a pan housing the non-fragmented cosmetic material, wherein the kit, comprises:
   a foamable liquid composition configured to be dispensed and used as a foam for physical contact with the broken cosmetic material, wherein the foamable liquid composition comprises, at least:
      (a) *Hamamelis virginiana,*
      (b) isopropyl alcohol, and
      (c) decyl glucoside;
   a dispenser configured for dispensing a foam, wherein the dispenser houses at least some of the foamable liquid composition;
   a spreading implement; and
   at least one pressing implement, wherein the at least one pressing implement comprises two opposing flat face surfaces and a grip, wherein the grip is disposed between each of the two opposing flat face surfaces, wherein the two opposing flat face surfaces are configured for pressing flatly against the broken cosmetic material when broken cosmetic material is dry.

9. The kit according to claim 8, wherein the foamable liquid composition comprises:
   (a) the *Hamamelis virginiana* in about 70.00 to about 90.00 wt. % of the foamable liquid composition;
   (b) the isopropyl alcohol in about 10.00 to about 30.00 wt. % of the foamable liquid composition; and
   (c) the decyl glucoside in about 0.50 to about 5.00 wt. % of the foamable liquid composition.

10. The kit according to claim 8, wherein the foamable liquid composition further comprises a fragrance and at least one carrier oil for the fragrance.

11. The kit according to claim 8, wherein the foamable liquid composition further comprises:
   lavender essential oil in about 0.01 to about 0.20 wt. % of the foamable liquid composition;
   jojoba oil in about 0.01 to about 0.20 wt. % of the foamable liquid composition;
   fractionated coconut oil in about 0.01 to about 0.20 wt. % of the foamable liquid composition; and
   vitamin E in about 0.01 to about 0.20 wt. % of the foamable liquid composition.

12. The kit according to claim 8, wherein the spreading implement is a spatula.

13. The kit according to claim 8, wherein the at least one pressing implement is a tamper, wherein the grip is an elongate member that is attached to both of the two opposing flat face surfaces.

14. The kit according to claim 8, wherein the two opposing flat face surfaces are each of a different size, wherein transverse width cross sections of the two opposing flat face surfaces are each larger than a transverse width cross section through the gripe.

15. The kit according to claim 8, wherein the two opposing flat face surfaces are each bounded by its own round perimeter.

16. The kit according to claim 8, wherein the two opposing flat face surfaces are each bounded by its own quadrilateral perimeter.

17. The kit according to claim 8, wherein at least one of the two opposing flat face surfaces is textured configured for imprinting that texture.

18. The kit according to claim 8, wherein the at least one pressing implement is two different pressing implements, wherein the two different pressing implements have different shapes with respect to each other.

* * * * *